United States Patent [19]

Grammenos et al.

[11] Patent Number: 5,430,172
[45] Date of Patent: Jul. 4, 1995

[54] PREPARATION OF 4-ALKANOYLARYL BENZYL ETHERS

[75] Inventors: Wassilios Grammenos, Ludwigshafen; Wolfgang Siegel, Mannheim; Klaus Oberdorf, Heidelberg; Bernd Mueller, Frankenthal; Hubert Sauter, Mannheim; Reinhard Doetzer, Weinheim, all of Germany

[73] Assignee: BASF Aktiengesellschaft, Ludwigshafen, Germany

[21] Appl. No.: 228,379

[22] Filed: Apr. 15, 1994

[30] Foreign Application Priority Data

Apr. 19, 1993 [DE] Germany ............... 43 12 637.5

[51] Int. Cl.$^6$ ............... C07C 41/48; C07C 45/61; C07C 231/12; C07C 249/12
[52] U.S. Cl. ............... 560/35; 558/239; 558/240; 558/414; 558/415; 560/51; 560/53; 564/165; 564/169; 564/256; 568/309; 568/314; 568/315; 568/316
[58] Field of Search ............... 560/35, 51, 53; 564/169, 165

[56] References Cited

U.S. PATENT DOCUMENTS

| | | | |
|---|---|---|---|
| 4,960,943 | 10/1990 | Botta et al. | 568/319 |
| 5,294,578 | 3/1994 | Ho et al. | 502/62 |
| 5,298,527 | 3/1994 | Grammenos et al. | 514/539 |

FOREIGN PATENT DOCUMENTS 0334096  9/1989  European Pat. Off.

OTHER PUBLICATIONS

Olah, G., *Friedel–Crafts and Related Reactions*, vol. I (1963) John Wiley and Sons, New York, pp. 102, 327–330, and 342–344.
Olah, G., *Friedel–Crafts and Related Reactions*, vol. III (1964) John Wiley and Sons, New York pp. 48–54 and 180–189.
Eugen Mueller, "Methoden der Organischen Chemie (Houven-Weyl) Band VII/2a", 1973, Georg Thieme Verlag, Stuttgart, pp. 15–18.
Houben-Weyl, Methoden der organischen Chemie, vol. 6/3, p. 146, Table 13 and p. 151, Georg Thieme Verlag, Stuttgart 1965.
Synthesis, 1972, D. E. Pearson, et al., "Friedel–Crafts Acylations With Little or No Catalyst", pp. 533–542.

*Primary Examiner*—Peter O'Sullivan
*Attorney, Agent, or Firm*—Oblon, Spivak, McClelland, Maier, & Neustadt

[57] ABSTRACT

A process for preparing 4-alkanoylaryl benzyl ethers of the general formula I

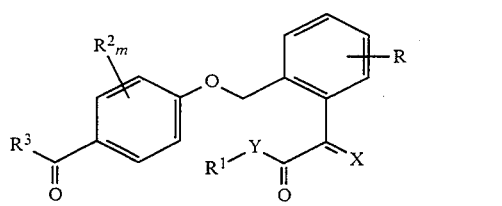

where
R is hydrogen, halogen, cyano; alkyl, alkoxy;
X is $CH_2$, $CH-CH_3$, $CH-CH_2-CH_3$, $CH-OCH_3$ or $N-OCH_3$;
Y is oxygen, sulfur, direct linkage or nitrogen;
m is 0, 1, 2 or 3;
$R^1$ is hydrogen; alkyl, alkenyl, alkynyl or alkoxy;
$R^2$ is cyano, halogen, alkyl, alkoxy or haloalkyl;
$R^3$ is alkyl; haloalkyl; cycloalkyl; or an unsubstituted or substituted mono- to trinuclear aromatic system, comprises reacting an aryl benzyl ether of the general formula II

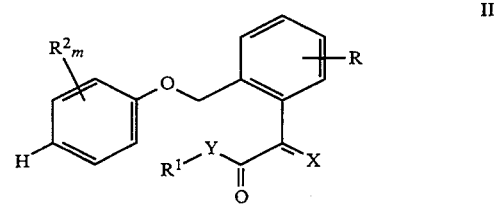

where X, Y, R, $R^1$, $R^2$ and m have the abovementioned meanings, with a carbonyl halide or with a carboxylic anhydride or with a carboxylic sulfonic anhydride in the presence of an acid and in the presence or absence of a diluent.

7 Claims, No Drawings

PREPARATION OF 4-ALKANOYLARYL BENZYL ETHERS

A process for preparing 4-alkanoylaryl benzyl ethers of the general formula I

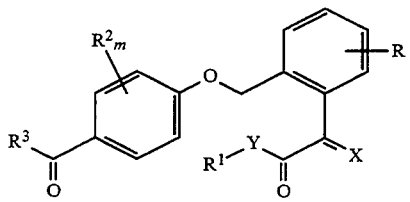

where
- R is hydrogen, halogen, cyano; $C_1$-$C_4$-alkyl, $C_1$-$C_4$-alkoxy;
- X is $CH_2$, CH—$CH_3$, CH—$CH_2$—$CH_3$, CH—$OCH_3$ or N—$OCH_3$;
- Y is oxygen, sulfur, direct linkage or nitrogen which can carry a hydrogen atom, a $C_1$-$C_4$-alkyl group or a $C_1$-$C_4$-alkoxy group;
- m is 0, 1, 2 or 3, it being possible for the $R^2$ radicals to be different when m is 2 or 3;
- $R^1$ is hydrogen; $C_1$-$C_5$-alkyl, $C_3$-$C_5$-alkenyl, $C_3$-$C_5$-alkynyl or $C_1$-$C_4$-alkoxy, it being possible for these groups to carry one or two halogen atoms;
- $R^2$ is cyano, halogen, $C_1$-$C_4$-alkyl, $C_1$-$C_4$-alkoxy or $C_1$-$C_4$-haloalkyl;
- $R^3$ is $C_1$-$C_{12}$-alkyl; $C_1$-$C_{12}$-haloalkyl; $C_3$-$C_8$-cycloalkyl; or an unsubstituted or substituted mono- to trinuclear aromatic system which may, besides carbon atoms, contain one to four nitrogen atoms or one to three hetero atoms selected from a group comprising two nitrogen atoms and one oxygen or sulfur atom, it also being possible for the aromatic radicals to carry one to three substituents selected from a group comprising halogen; $C_1$-$C_4$-alkyl; $C_1$-$C_4$-alkoxy, in which the ethers of the formula I where $R^3$—CO is H are reacted with carbonyl halides or carboxylic anhydrides in the presence of an acid. The acids act as catalysts.

Numerous processes for acylating phenyl alkyl ethers have been disclosed. Conventional methods are reviewed in the following references:
1. G. A. OLAH, Friedel-Crafts and related reactions, vol. III, pages 48–51, 180–189, John Wiley and Sons Inc. New York, 1964
2. D. E. PEARSON, C. A. BUEHLER, Synthesis 1972, 533–542.

These processes are not suitable for acylating aryl benzyl ethers of the formula II because there is preferential cleavage of the benzyl ether under the reaction conditions. This is described in Houben-Weyl, Methoden der organischen Chemie, vol. 6/3, page 146 Table 13 and page 151 lines 24 et seq., Georg Thieme Verlag, Stuttgart 1965. It has also emerged from our own comparative experiments.

The acylated aryl benzyl ethers are obtained only in very low yield by known processes. In the case of the starting materials of the formula II there must also be expected to be yield-reducing side reactions owing to the presence of the $R^1$—Y—CO—CX— functional groups.

It is an object of the present invention to improve the accessibility of the compounds I.

We have found that this object is achieved by a novel process for preparing 4-alkanoylaryl benzyl ethers and 4-aroylaryl benzyl ethers of the formula I which provides surprisingly high yields and which comprises acylating aryl benzyl ethers of the formula II under the reaction conditions described hereinafter;

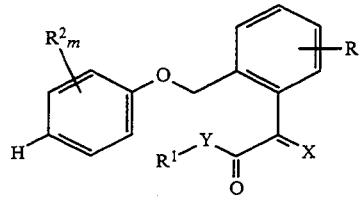

When carbonyl halides are used as acylating agents in stoichiometric amount based on the compound of the formula II or in an excess of up to 10 mole equivalents above the stoichiometric amount, examples of the catalysts used are Lewis acids, eg. $AlBr_3$, $ZnBr_2$, $SnCl_4$, $FeCl_3$, $FeBr_3$, $GaCl_3$, $TiCl_4$, $InCl_3$ and $BF_3$ in amounts of from 1 to 5 mole equivalents of acid based on the compound II. The chosen reaction temperature is, for example, in the range from $-80°$ C. to $25°$ C., preferably from $-50°$ C. to $0°$ C.

When carboxylic anhydrides or carboxylic sulfonic anhydrides are used in stoichiometric amount based on the compound of the formula II or in an excess of up to 30 mole equivalents above the stoichiometric amount, examples of catalysts used are Lewis or Brönsted acids in amounts of from 1 to 5 mole equivalents of acid based on the compound II. The chosen reaction temperature is, for example, in the range from $0°$ C. to $140°$ C., preferably from $20°$ C. to $80°$ C.

Examples of suitable diluents are inert hydrocarbons such as pentane, hexane, heptane, octane or chlorinated hydrocarbons such as dichloromethane, 1,2-dichloroethane, chlorobenzene, 1,2-dichlorobenzene, 1,3-dichlorobenzene, 1,4-dichlorobenzene or dipolar aprotic solvents such as acetonitrile, nitromethane, nitrobenzene or alkyl esters of alkanoic and arylcarboxylic acids such as methyl acetate, ethyl acetate, propyl acetate, methyl benzoate or ethyl benzoate.

The aryl benzyl ethers II used as starting materials are known, and their preparation is described (cf. EP 178 826, EP 253 213, EP 254 426, EP 280 185, EP 336 211, EP 348 766, EP 498 188, EP 398 692 and EP 493 711).

The preparation process according to the invention can be used successfully to synthesize the compounds I according to the definition, in particular for preparing those compounds in which the variables have the following meanings:
- R is hydrogen, halogen such as fluorine, chlorine, bromine and iodine, in particular fluorine and chlorine; cyano; $C_1$-$C_4$-alkyl such as methyl, ethyl, isopropyl and n-propyl, especially methyl and ethyl; $C_1$-$C_4$-alkoxy such as methoxy, ethoxy, 1-methylethoxy and n-propoxy, in particular methoxy and ethoxy;
- X is $CH_2$, CH—$CH_3$, CH—$CH_2CH_3$, CH—$OCH_3$ and N—$OCH_3$;
- Y is oxygen, sulfur, a direct linkage or nitrogen which can carry a hydrogen atom, a $C_1$-$C_4$-alkyl group as specified above in general and in particular, or a $C_1-C_4$-alkoxy group as specified above in general and in particular;

m is 0, 1, 2 or 3, it being possible for the $R^2$ radicals to be different when m is 2 or 3;

$R^1$ is hydrogen; $C_1-C_5$-alkyl, especially $C_1-C_4$-alkyl as specified above in general and in particular; $C_3-C_5$-alkenyl such as 1-propenyl, 2-propenyl, 1-methylethenyl, 1-butenyl, 2-butenyl, 3-butenyl, 3-methyl-2-butenyl, especially 2-propenyl, 2-butenyl and 3-methyl-2-butenyl; $C_3-C_5$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, especially 2-propynyl and 2-butynyl, $C_1-C_4$-alkoxy such as methoxy, ethoxy, 1-propoxy, 2-propoxy, 2-methyl-1-propoxy; 2-methyl-2-propoxy, 1-butoxy and 2-butoxy, it being possible for these hydrocarbon groups to carry one or two halogen atoms such as fluorine, chlorine, bromine and iodine, in particular fluorine and chlorine;

$R^1$ is additionally vinyl or ethynyl, if Y is a direct linkage;

$R^2$ is cyano; halogen as specified above in general and in particular; $C_1-C_4$-alkyl as specified above in general and in particular; $C_1-C_4$-alkoxy as specified above in general and in particular; $C_1-C_4$-haloalkyl, especially $C_1-C_2$-haloalkyl such as chloromethyl, dichloromethyl, trichloromethyl, fluoromethyl, difluoromethyl, trifluoromethyl, especially trifluoromethyl;

$R^3$ is $C_1-C_{12}$-alkyl, especially $C_1-C_7$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, heptyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropoxy, 1,2,2-trimethylpropyl, 1-ethyl-1-methylpropyl, 1-ethyl-2-methylpropyl;

$C_1-C_{12}$-haloalkyl, especially $C_1-C_7$-haloalkyl such as chloromethyl, bromomethyl, fluoromethyl, trichloromethyl, trifluoromethyl, difluoromethyl, 2-chloroethyl, 2-bromoethyl, 2-fluoromethyl, 2,2,2-trichloroethyl, 3-chloropropyl, 3-bromopropyl, 4-chlorobutyl, 4-bromobutyl, 1-chloroethyl, 1-bromoethyl, 1-fluoroethyl, 5-chloropentyl, 5-bromopentyl, 6-chlorohexyl, 6-bromohexyl, 7-chloroheptyl and 7-bromoheptyl;

$C_3-C_8$-cycloalkyl, especially $C_3-C_6$-cycloalkyl, such as cyclopropyl, cyclobutyl, cyclopentyl and cyclohexyl;

an unsubstituted or substituted mono- to trinuclear aromatic system which may, besides carbon atoms, contain one to four nitrogen atoms or one or two nitrogen atoms and one oxygen or sulfur atom, especially phenyl, 1-naphthyl, 2-naphthyl, 1-anthryl, 2-anthryl, 9-anthryl, 9-fluorenyl and 2-fluorenyl, in particular phenyl, five-membered heteroaromatic rings containing one to three hetero atoms selected from a group comprising three nitrogen atoms and one oxygen or sulfur atom, such as 2-furyl, 3-furyl, 2-thienyl, 3-thienyl, 1-pyrrolyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-triazol-2-yl, 1,3,4-oxadiazol-2-yl, 1,3,4-thiadiazol-2-yl, 1,3,4-triazol-2-yl, 1,2,3-oxadiazol-4-yl, 1,2,3-oxadiazol-5-yl, 1,2,5-triazol-3-yl, 1,2,3-triazol-4-yl, 1,2,3-triazol-5-yl, 1,2,3-triazol-4-yl, 5-tetrazolyl, 1,2,3,4-thiatriazol-5-yl and 1,2,3,4-oxatriazol-5-yl, in particular 3-pyrrolyl, 3-isoxazolyl, 5-isoxazolyl, 4-oxazolyl, 4-thiazolyl, 4-pyrazolyl, 5-pyrazolyl, 1,3,4-oxadiazol-2-yl and 1,3,4-thiadiazol-2-yl, six-membered heteroaromatic rings containing one to four nitrogen atoms as hetero atoms such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl, in particular 2-pyridinyl, 3-pyridinyl, 2-pyrimidinyl, 4-pyrimidinyl and 1,3,5-triazin-2-yl, it being possible for these groups to carry one to three halogen atoms such as chlorine, fluorine, bromine and iodine, in particular chlorine and fluorine, and/or one to three $C_1-C_4$-alkyl radicals as specified above in general and in particular, and/or one to three $C_1-C_4$-alkoxy radicals as specified above in general and in particular.

The ketones of the general formula I are valuable intermediates for synthesizing E- and Z-oxime ethers of the general formula III which are used as pesticides, in particular as fungicides, for protecting crops (cf. DE 3937 457, EP 513 580, EP 498 188)

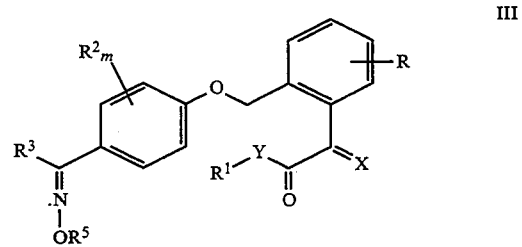

III where $R^5$ is $C_1-C_6$-alkyl, $C_2-C_6$-alkenyl and $C_2-C_6$-alkynyl, it being possible for these radicals to carry one to three halogen atoms and/or one to three of the following radicals:

cyano; nitro; $C_1-C_6$-alkoxy, $C_1-C_6$-alkylthio and $C_3-C_6$-cycloalkyl; $R^5$ is additionally a 5- or 6-membered aromatic system, preferably phenyl, which in turn can carry one to three substituents selected from a group comprising halogen, cyano, nitro, $C_1-C_4$-alkyl and $C_1-C_4$-alkoxy.

The final products III can be prepared by conventional processes and methods starting from the ketones of the formula I (cf. DE 39 37 457, EP 513 580, EP 498 188).

Comparative Experiments

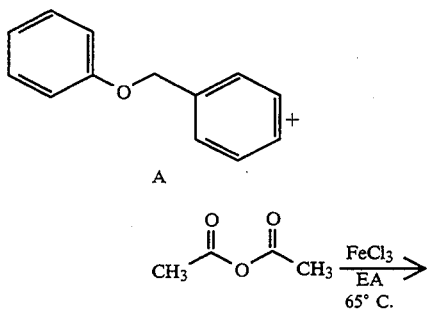

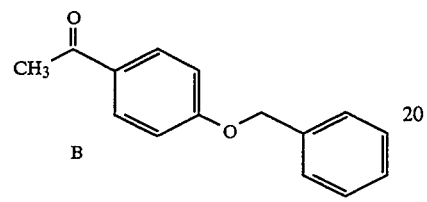

9.21 g (50 mmol) of benzyl phenyl ether A and 10.21 g (100 mmol) of acetic anhydride (Ac$_2$O) are added dropwise to a solution of 2.43 g (15 mmol) of FeCl$_3$ in 50 ml ethyl acetate while stirring at 65° C. After 1 h, the mixture is analyzed by gas chromatography (GC). Result: unselective reaction, 80% of the benzyl phenyl ether consumed but the reaction mixture contains less than 1% of compound B.

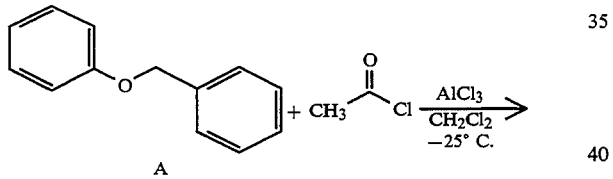

zyl phenyl ether A consumed but the reaction mixture contains less than 1% compound B.

General method for the acylation according to the invention with AlCl$_3$

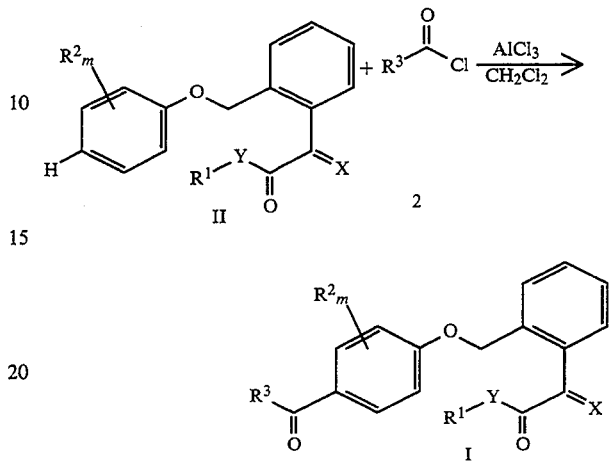

75 mmol of AlCl$_3$ are introduced into 75 ml of CH$_2$Cl$_2$ at −15° C. 75 mmol of acid chloride 2 are added dropwise at −15° C. over the course of 15 min. The mixture is cooled to −20° to −25° C. and a solution of 30 mmol of aryl benzyl ether II in 20 ml of CH$_2$Cl$_2$ is added dropwise. The mixture is then stirred for 1 h and hydrolyzed on 200 g of ice, 150 ml of CH$_2$Cl$_2$ are added, and the phases are separated. Drying over Na$_2$SO$_4$ is followed by concentration under reduced pressure and recrystallization of the residue. Compound I is obtained.

The following results were obtained by the method described above.

| X | R$^2_m$ | R$^3$ | Y−R$^1$ | Solvent for crystallizations | Yield of Compound I based on Compound II |
|---|---|---|---|---|---|
| NOCH$_3$ | 2-CH$_3$ | CH$_3$ | OCH$_3$ | toluene/heptane = 1/1, | 85% |
| NOCH$_3$ | 2-CH$_3$ | C$_2$H$_5$ | OCH$_3$ | toluene/heptane = 1/2 | 82% |
| NOCH$_3$ | 2-CH$_3$ | ClCH$_2$CH$_2$ | OCH$_3$ | CH$_3$OH | 58% |
| NOCH$_3$ | 2-CH$_3$ | ClCH$_2$CH$_2$CH$_2$ | OCH$_3$ | CH$_3$OH | 65% |
| NOCH$_3$ | 2-CH$_3$ | ClCH$_2$CH$_2$CH$_2$CH$_2$ | OCH$_3$ | CH$_3$OH | 70% |
| NOCH$_3$ | 2-CH$_3$ | Ph | OCH$_3$ | toluene/heptane = 1/2.5 | 81% |
| NOCH$_3$ | 2,5-(CH$_3$)$_2$ | CH$_3$ | OCH$_3$ | toluene/heptane = 1/2 | 83% |
| NOCH$_3$ | 2-CH$_3$ | CH$_3$ | NHCH$_3$ | toluene/heptane = 1/2 | 91% |

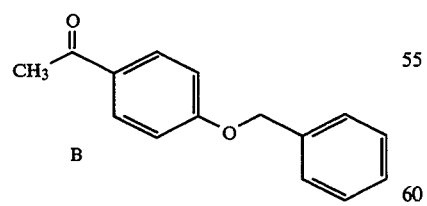

4 g (30 mmol) of AlCl$_3$ are introduced into 25 ml of CH$_2$Cl$_2$ at −25° C. while stirring. At −25° C., 2.40 g (30 mmol) of acetyl chloride (AcCl) are added dropwise. After 15 min, 5.53 g (30 mmol) of benzyl phenyl ether A in 10 ml of CH$_2$Cl$_2$ are added dropwise.

After 1 h, the mixture is hydrolyzed and analyzed by GC. Result: completely unselective reaction. 83% ben- Catalytic acylation with FeCl$_3$

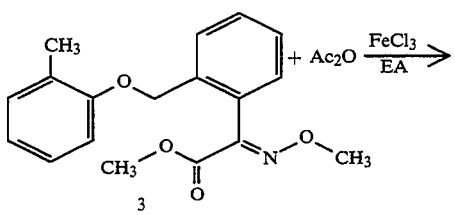

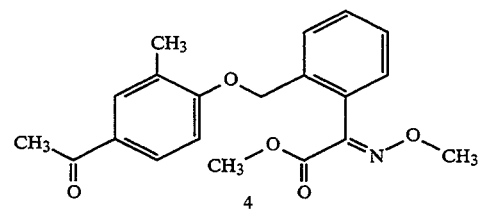

490 mg (3 mmol) of FeCl₃ are introduced into 10 ml of ethyl acetate at 65° C. A mixture of 3.13 g (10 mmol) of aryl benzyl ether 3 and 2.04 g (20 mmol) of Ac₂O in 10 ml of ethyl acetate is added dropwise. After 16 h at 65° C., the mixture is concentrated under reduced pressure and the residue is chromatographed on silica gel. 2.42 g of compound 4 are obtained in 68% yield.

The compounds specified in the following tables are obtained in a corresponding way.

TABLE I

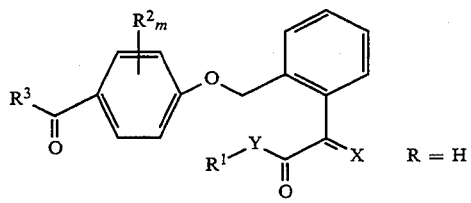

R = H

| Comp. No. | $R^3$ | $R^1$—Y | X | $R^2_m$ | Physic. data [IR (cm$^{-1}$); NMR (ppm) mp (°C.)] |
|---|---|---|---|---|---|
| 1 | CH₃ | OCH₃ | NOCH₃ | 2-CH₃ | 120–122° C. |
| 2 | CH₂CH₃ | OCH₃ | NOCH₃ | 2-CH₃ | 106–108° C. |
| 3 | CH₃ | OCH₃ | CH—CH₃ | 2-CH₃ | 96–98° C. |
| 4 | CH₃ | NH—CH₃ | NOCH₃ | 2-CH₃ | 115–116° C. |
| 5 | cyclopropyl | NH—CH₃ | NOCH₃ | 2-CH₃ | 7.9–6.8(m, 7H), 6.78(m, 1H), 5.0(S, 2H), 3.95 (S, 3H), 2.9(d, 3H), 2.6(m, 1H), 2.2(S, 3H), 1.2–0.82(m, 4H) |
| 6 | CH₂CH₂—Cl | OCH₃ | NOCH₃ | 2-CH₃ | 121–122° C. |
| 7 | CH₂CH₂CH₂—Cl | OCH₃ | NOCH₃ | 2-CH₃ | 103–104° C. |
| 8 | CH₂CH₂CH₂CH₂—Cl | OCH₃ | NOCH₃ | 2-CH₃ | 108–109° C. |
| 9 | phenyl | OCH₃ | NOCH₃ | 2-CH₃ | 141–143° C. |
| 10 | CH₃ | OCH₃ | NOCH₃ | 2,5-(CH₃)₂ | 112–114° C. |
| 11 | CH₃ | NHCH₃ | NOCH₃ | 2,5-(CH₃)₂ | 143–145° C. |
| 12 | CH₃ | OCH₃ | CHCH₃ | 2,5-(CH₃)₂ | 62–64° C. |
| 13 | CH₃ | OCH₃ | CHCH₂CH₃ | 2,5-(CH₃)₂ | 1716, 1672, 1258, 1140, 1050 |
| 14 | CH₃ | OCH₃ | NOCH₃ | 2-Cl | 119–121° C. |
| 15 | CH₃ | NH—CH₃ | NOCH₃ | 2-Cl | 124–126° C. |
| 16 | CH₂CH₂CH₃ | OCH₃ | NOCH₃ | 2-CH₃ | 102–105° C. |
| 17 | CH(CH₃)₂ | OCH₃ | NOCH₃ | 2-CH₃ | 105–107° C. |
| 18 | CH₂CH₃ | OCH₃ | NOCH₃ | 2,5-(CH₃)₂ | 87–89° C. |
| 19 | phenyl | NHCH₃ | NOCH₃ | 2-CH₃ | 1670, 1650, 1599, 1500, 1269, 1119, 1035, 976 |
| 20 | CH₂CH₃ | OCH₃ | CH—CH₃ | 2-CH₃ | 7.8–7.05(m, 8H), 6.8 (d, 1H), 5.0(s, 2H), 3.9 (s, 3H), 2.9(q, 2H), 2.3 (s, 3H), 1.7(d, 3H), 1.1(t, 3H) |
| 21 | CH(CH₃)₂ | OCH₃ | CH—CH₃ | 2-CH₃ | 1716, 1599, 1251, 1131 |
| 22 | CH₂CH₃ | OCH₃ | CHCH₂CH₃ | 2-CH₃ | 70–74° C. |
| 23 | CH₂CH₃ | NHCH₃ | CH—CH₃ | 2-CH₃ | 1672, 1600, 1253, 1234 |
| 24 | CH₃ | NHCH₃ | CH—CH₃ | 2,5(CH₃)₂ | 1664, 1260, 1143 |
| 25 | CH₂CH₃ | OCH₃ | CH—CH₃ | 2,5-(CH₃)₂ | 66–67° C. |
| 26 | CH₂CH₃ | NHCH₃ | NOCH₃ | 2,5-(CH₃)₂ | 121–123° C. |
| 27 | CH₃ | OCH₃ | CHCH₃ | 2-Cl | 1717, 1674, 1278, 1247 |
| 28 | CH₃ | OCH₃ | NOCH₃ | 2-CH₃-5-Cl | 1739, 1597, 1251, 1068, 1008 |
| 29 | CH₃ | OCH₃ | CHCH₃ | 2-CH₃-5-Cl | 1716, 1598, 1255, 1174 |
| 30 | CH₃ | NHCH₃ | NOCH₃ | 2-CH₃-5-Cl | 1667, 1598, 1254, 1037, 987 |
| 31 | CH₂—CH(CH₃)₂ | NHCH₃ | NOCH₃ | 2-CH₃ | 6.7–7.8(m, 8H), 5.05 |

TABLE -continued

I

| Comp. No. | R³ | R¹—Y | X | R²ₘ | Physic. data [IR (cm⁻¹); NMR (ppm) mp (°C.)] |
|---|---|---|---|---|---|
| 32 | C(CH₃)₃ | NHCH₃ | NOCH₃ | 2-CH₃ | (s, 2H), 3.9(s, 3H), 2.9 (d, 3H), 2.3(s, 3H) and 1.0(d, 6H) 1665, 1600, 1528, 1255, 1129, 1037 |
| 33 | cyclopentyl | NHCH₃ | NOCH₃ | 2-CH₃ | 7.8–6.7(m, 8H), 5.05 (s, 2H), 3.95(s, 3H), 2.9(d, 3H), 2.3(s, 3H), 1.9–1.6(m, 9H) |
| 34 | CH₃ | NHCH₃ | NOCH₃ | 2,3,5-(CH₃)₃ | 126° C. |

Table 1

Compounds of the formula I.1 where Y—R¹ is methoxy and the combination of the substituents R³ and X for a compound in each case corresponds to one line of one column in Table A

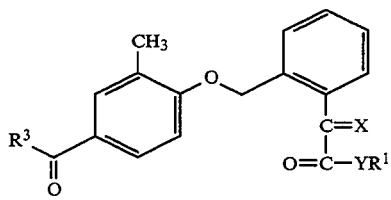

I.1

Table 2

Compounds of the formula I.2 where Y—R¹ is methylamino and the combination of the substituents R³ and X for a compound in each case corresponds to one line of one column in Table A.

Table 3

Compounds of the formula I.2 where Y—R¹ is methoxy and the combination of the substituents R³ and X for a compound in each case corresponds to one line of one column in Table A.

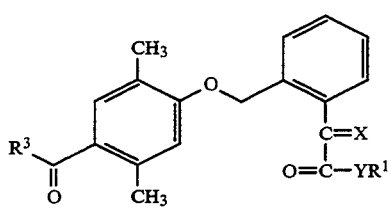

I.2

Table 4

Compounds of the formula I.2 where Y—R¹ is methylamino and the combination of the substituents R³ and X for a compound in each case corresponds to one line of one column in Table A.

Table 5

Compounds of the formula I.3 where Y—R¹ is methoxy and the combination of the substituents R³ and X for a compound in each case corresponds to one line of one column in Table A.

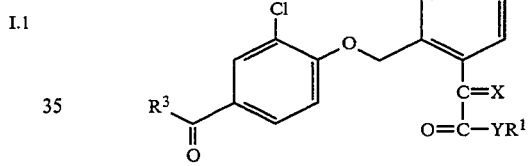

I.3

Table 6

Compounds of the formula I.3 where Y—R¹ is methylamino and the combination of the substituents R³ and X for a compound in each case corresponds to one line of one column in Table A.

Table 7

Compounds of the formula I.4 where Y—R¹ is methoxy and the combination of the substituents R³ and X for a compound in each case corresponds to one line of one column in Table A.

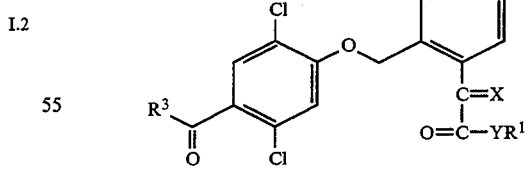

I.4

Table 8

Compounds of the formula I.4 where Y—R¹ is methylamino and the combination of the substituents R³ and X for a compound in each case corresponds to one line of one column in Table A.

Table 9

Compounds of the formula I.5 where Y—R¹ is methoxy and the combination of the substituents R³ and X for a compound in each case corresponds to one line of one column in Table A.

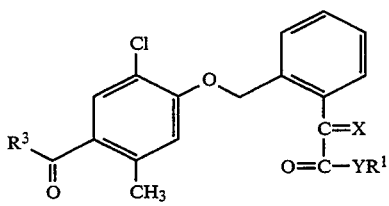

I.5

Table 10

Compounds of the formula I.5 where Y—$R^1$ is methylamino and the combination of the substituents $R^3$ and X for a compound in each case corresponds to one line of one column in Table A.

Table 11

Compounds of the formula I.6 where Y—$R^1$ is methoxy and the combination of the substituents $R^3$ and X for a compound in each case corresponds to one line of one column in Table A.

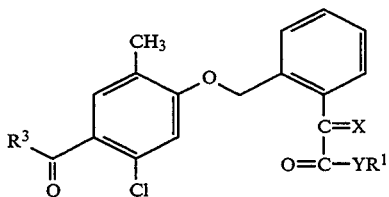

I.6

Table 12

Compounds of the formula I.6 where Y—$R^1$ is methylamino and the combination of the substituents $R^3$ and X for a compound in each case corresponds to one line of one column in Table A.

Table 13

Compounds of the formula I.7 where Y—$R^1$ is methoxy and the combination of the substituents $R^3$ and X for a compound in each case corresponds to one line of one column in Table A.

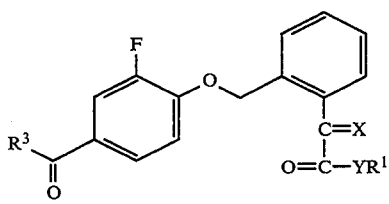

I.7

Table 14

Compounds of the formula I.7 where Y—$R^1$ is methylamino and the combination of the substituents $R^3$ and X for a compound in each case corresponds to one line of one column in Table A.

Table 15

Compounds of the formula I.1 where X is $NOCH_3$ and the combination of the substituents $YR^1$ and $R^3$ for a compound in each case corresponds to one line of one column In Table B.

Table 16

Compounds of the formula I.2 where X is $NOCH_3$ and the combination of the substituents $YR^1$ and $R^3$ for a compound in each case corresponds to one line of one column in Table B.

Table 17

Compounds of the formula I.3 where X is $NOCH_3$ and the combination of the substituents $YR^1$ and $R^3$ for a compound in each case corresponds to one line of one column in Table B.

Table 18

Compounds of the formula I.4 where X is $NOCH_3$ and the combination of the substituents $YR^1$ and $R^3$ for a compound in each case corresponds to one line of one column in Table B.

Table 19

Compounds of the formula I.5 where X is $NOCH_3$ and the combination of the substituents $YR^1$ and $R^3$ for a compound in each case corresponds to one line of one column in Table B.

Table 20

Compounds of the formula I.6 where X is $NOCH_3$ and the combination of the substituents $YR^1$ and $R^3$ for a compound in each case corresponds to one line of one column in Table B.

Table 21

Compounds of the formula I.7 where X is $NOCH_3$ and the combination of the substituents YR1 and $R^3$ for a compound in each case corresponds to one line of one column in Table B.

TABLE A

| $R^3$ | X |
|---|---|
| $CH_3$ | $CHOCH_3$ |
| $CH_3$ | $NOCH_3$ |
| $CH_3CH_2$ | $CHOCH_3$ |
| $CH_3CH_2$ | $NOCH_3$ |
| $CH_3CH_2CH_2$ | $CHOCH_3$ |
| $CH_3CH_2CH_2$ | $NOCH_3$ |
| $CH_3CH_2CH_2CH_2$ | $CHOCH_3$ |
| $CH_3CH_2CH_2CH_2$ | $NOCH_3$ |
| $CH_3(CH_2)_4$ | $CHOCH_3$ |
| $CH_3(CH_2)_4$ | $NOCH_3$ |
| $CH_3(CH_2)_5$ | $CHOCH_3$ |
| $CH_3(CH_2)_5$ | $NOCH_3$ |
| $CH_2$—Cl | $CHOCH_3$ |
| $CH_2$—Cl | $NOCH_3$ |
| $CH_2Br$ | $CHOCH_3$ |
| $CH_2Br$ | $NOCH_3$ |
| $CH_2CH_2Cl$ | $CHOCH_3$ |
| $CH_2CH_2Cl$ | $NOCH_3$ |
| $CH_2CH_2CH_2Cl$ | $CHOCH_3$ |
| $CH_2CH_2CH_2Cl$ | $NOCH_3$ |
| $CH_2(CH_2)_3$—Cl | $CHOCH_3$ |
| $CH_2(CH_2)_3$—Cl | $NOCH_3$ |
| $CH_2(CH_2)_4$—Cl | $CHOCH_3$ |
| $CH_2(CH_2)_4$—Cl | $NOCH_3$ |
| $CF_3$ | $CHOCH_3$ |
| $CF_3$ | $NOCH_3$ |
| $CF_2$—$CF_3$ | $CHOCH_3$ |
| $CF_2$—$CF_3$ | $NOCH_3$ |
| $CH_2CH_2Br$ | $CHOCH_3$ |
| $CH_2CH_2Br$ | $NOCH_3$ |
| $CH_2CH_2CH_2Br$ | $CHOCH_3$ |
| $CH_2CH_2CH_2Br$ | $NOCH_3$ |
| $CH_2(CH_2)_3$—Br | $CHOCH_3$ |
| $CH_2(CH_2)_3$—Br | $NOCH_3$ |
| $CH_2CF_3$ | $CHOCH_3$ |
| $CH_2CF_3$ | $NOCH_3$ |
| $CH_2$—$CH(CH_3)_2$ | $CHOCH_3$ |
| $CH_2$—$CH(CH_3)_2$ | $NOCH_3$ |
| $CH_2$—$C(CH_3)_3$ | $CHOCH_3$ |
| $CH_2$—$C(CH_3)_3$ | $NOCH_3$ |
| $CH(CH_3)_2$ | $CHOCH_3$ |
| $CH(CH_3)_2$ | $NOCH_3$ |
| t-Butyl | $CHOCH_3$ |
| t-Butyl | $NOCH_3$ |
| Phenyl | $CHOCH_3$ |
| Phenyl | $NOCH_3$ |
| 2-Pyridinyl | $CHOCH_3$ |
| 2-Pyridinyl | $NOCH_3$ |
| 3-Pyridinyl | $CHOCH_3$ |
| 3-Pyridinyl | $NOCH_3$ |
| 4-Pyridinyl | $CHOCH_3$ |
| 4-Pyridinyl | $NOCH_3$ |
| Cyclopropyl | $CHOCH_3$ |

TABLE A-continued

| R³ | X |
|---|---|
| Cyclopropyl | NOCH₃ |
| Cyclopentyl | CHOCH₃ |
| Cyclopentyl | NOCH₃ |
| Cyclohexyl | CHOCH₃ |
| Cyclohexyl | NOCH₃ |
| CH₃ | CHCH₃ |
| CH₃CH₂ | CHCH₂CH₃ |
| CH₃CH₂ | CHCH₃ |
| CH₃CH₂ | CHCH₂CH₃ |
| CH₃CH₂CH₂ | CHCH₃ |
| CH₃CH₂CH₂ | CHCH₂CH₃ |
| CH₃CH₂CH₂CH₂ | CHCH₃ |
| CH₃CH₂CH₂CH₂ | CHCH₂CH₃ |
| CH₃(CH₂)₄ | CHCH₃ |
| CH₃(CH₂)₄ | CHCH₂CH₃ |
| CH₃(CH₂)₅ | CHCH₃ |
| CH₃(CH₂)₅ | CHCH₂CH₃ |
| CH₂—Cl | CHCH₃ |
| CH₂—Cl | CHCH₂CH₃ |
| CH₂Br | CHCH₃ |
| CH₂Br | CHCH₂CH₃ |
| CH₂CH₂Cl | CHCH₃ |
| CH₂CH₂Cl | CHCH₂CH₃ |
| CH₂CH₂CH₂Cl | CHCH₃ |
| CH₂CH₂CH₂Cl | CHCH₂CH₃ |
| CH₂(CH₂)₃—Cl | CHCH₃ |
| CH₂(CH₂)₃—Cl | CHCH₂CH₃ |
| CH₂(CH₂)₄—Cl | CHCH₃ |
| CH₂(CH₂)₄—Cl | CHCH₂CH₃ |
| CF₃ | CHCH₃ |
| CF₃ | CHCH₂CH₃ |
| CF₂—CF₃ | CHCH₃ |
| CF₂—CF₃ | CHCH₂CH₃ |
| CH₂CH₂Br | CHCH₃ |
| CH₂CH₂Br | CHCH₂CH₃ |
| CH₂CH₂CH₂Br | CHCH₃ |
| CH₂CH₂CH₂Br | CHCH₂CH₃ |
| CH₂(CH₂)₃—Br | CHCH₃ |
| CH₂(CH₂)₃—Br | CHCH₂CH₃ |
| CH₂CF₃ | CHCH₃ |
| CH₂CF₃ | CHCH₂CH₃ |
| CH₂—CH(CH₃)₂ | CHCH₃ |
| CH₂—CH(CH₃)₂ | CHCH₂CH₃ |
| CH₂—C(CH₃)₃ | CHCH₃ |
| CH₂—C(CH₃)₃ | CHCH₂CH₃ |
| CH(CH₃)₂ | CHCH₃ |
| CH(CH₃)₂ | CHCH₂CH₃ |
| t-Butyl | CHCH₃ |
| t-Butyl | CHCH₂CH₃ |
| Phenyl | CHCH₃ |
| Phenyl | CHCH₂CH₃ |
| 2-Pyridinyl | CHCH₃ |
| 2-Pyridinyl | CHCH₂CH₃ |
| 3-Pyridinyl | CHCH₃ |
| 3-Pyridinyl | CHCH₂CH₃ |
| 4-Pyridinyl | CHCH₃ |
| 4-Pyridinyl | CHCH₂CH₃ |
| Cyclopropyl | CHCH₃ |
| Cyclopropyl | CHCH₂CH₃ |
| Cyclopentyl | CHCH₃ |
| Cyclopentyl | CHCH₂CH₃ |
| Cyclohexyl | CHCH₃ |
| Cyclohexyl | CHCH₂CH₃ |

TABLE B

| R³ | Y—R¹ |
|---|---|
| CH₃ | NH—CH₃ |
| CH₃ | N(CH₃)₂ |
| CH₃CH₂ | NH—CH₃ |
| CH₃CH₂ | N(CH₃)₂ |
| CH₃CH₂CH₂ | NH—CH₃ |
| CH₃CH₂CH₂ | N(CH₃)₂ |
| CH₃CH₂CH₂CH₂ | NH—CH₃ |
| CH₃(CH₂)₄ | NH—CH₃ |
| CH₃(CH₂)₄ | N(CH₃)₂ |
| CH₃(CH₂)₅ | NH—CH₃ |
| CH₃(CH₂)₅ | N(CH₃)₂ |
| CH₂—Cl | NH—CH₃ |

TABLE B-continued

| R³ | Y—R¹ |
|---|---|
| CH₂—Cl | N(CH₃)₂ |
| CH₂Br | NH—CH₃ |
| CH₂Br | N(CH₃)₂ |
| CH₂CH₂Cl | NH—CH₃ |
| CH₂CH₂Cl | N(CH₃)₂ |
| CH₂CH₂CH₂Cl | NH—CH₃ |
| CH₂CH₂CH₂Cl | N(CH₃)₂ |
| CH₂(CH₂)₃—Cl | NH—CH₃ |
| CH₂(CH₂)₃—Cl | N(CH₃)₂ |
| CH₂(CH₂)₄—Cl | NH—CH₃ |
| CH₂(CH₂)₄—Cl | N(CH₃)₂ |
| CF₃ | NH—CH₃ |
| CF₃ | N(CH₃)₂ |
| CF₂—CF₃ | NH—CH₃ |
| CF₂—CF₃ | N(CH₃)₂ |
| CH₂CH₂Br | NH—CH₃ |
| CH₂CH₂Br | N(CH₃)₂ |
| CH₂CH₂CH₂Br | NH—CH₃ |
| CH₂CH₂CH₂Br | N(CH₃)₂ |
| CH₂(CH₂)₃—Br | NH—CH₃ |
| CH₂(CH₂)₃—Br | N(CH₃)₂ |
| CH₂CF₃ | NH—CH₃ |
| CH₂CF₃ | N(CH₃)₂ |
| CH₂—CH(CH₃)₂ | NH—CH₃ |
| CH₂—CH(CH₃)₂ | N(CH₃)₂ |
| CH₂—C(CH₃)₃ | NH—CH₃ |
| CH₂—C(CH₃)₃ | N(CH₃)₂ |
| CH(CH₃)₂ | NH—CH₃ |
| CH(CH₃)₂ | N(CH₃)₂ |
| t-Butyl | NH—CH₃ |
| t-Butyl | N(CH₃)₂ |
| Phenyl | NH—CH₃ |
| Phenyl | N(CH₃)₂ |
| 2-Pyridinyl | NH—CH₃ |
| 2-Pyridinyl | N(CH₃)₂ |
| 3-Pyridinyl | NH—CH₃ |
| 3-Pyridinyl | N(CH₃)₂ |
| 4-Pyridinyl | NH—CH₃ |
| 4-Pyridinyl | N(CH₃)₂ |
| Cyclopropyl | NH—CH₃ |
| Cyclopropyl | N(CH₃)₂ |
| Cyclopentyl | NH—CH₃ |
| Cyclopentyl | N(CH₃)₂ |
| Cyclohexyl | NH—CH₃ |
| Cyclohexyl | N(CH₃)₂ |
| CH₃ | CH₃ |
| CH₃ | CH₃CH₃ |
| CH₃CH₂ | CH₃ |
| CH₃CH₂ | CH₂CH₃ |
| CH₃CH₂ | CH₃ |
| CH₃CH₂CH₂ | CH₂CH₃ |
| CH₃CH₂CH₂CH₂ | CH₃ |
| CH₃CH₂CH₂CH₂ | CH₂CH₃ |
| CH₃(CH₂)₄ | CH₃ |
| CH₃(CH₂)₄ | CH₂CH₃ |
| CH₃(CH₂)₅ | CH₃ |
| CH₃(CH₂)₅ | CH₂CH₃ |
| CH₂—Cl | CH₃ |
| CH₂—Cl | CH₂CH₃ |
| CH₂Br | CH₃ |
| CH₂Br | CH₂CH₃ |
| CH₂CH₂Cl | CH₃ |
| CH₂CH₂Cl | CH₂CH₃ |
| CH₂CH₂CH₂Cl | CH₃ |
| CH₂CH₂CH₂Cl | CH₂CH₃ |
| CH₂(CH₂)₃—Cl | CH₃ |
| CH₂(CH₂)₃—Cl | CH₂CH₃ |
| CH₂(CH₂)₄—Cl | CH₃ |
| CH₂(CH₂)₄—Cl | CH₂CH₃ |
| CF₃ | CH₃ |
| CF₃ | CH₂CH₃ |
| CF₂—CF₃ | CH₃ |
| CF₂—CF₃ | CH₂CH₃ |
| CH₂CH₂Br | CH₃ |
| CH₂CH₂Br | CH₂CH₃ |
| CH₂CH₂CH₂Br | CH₃ |
| CH₂CH₂CH₂Br | CH₂CH₃ |
| CH₂(CH₂)₃—Br | CH₃ |
| CH₂(CH₂)₃—Br | CH₂CH₃ |
| CH₂CF₃ | CH₃ |

TABLE B-continued

| R³ | Y—R¹ |
|---|---|
| CH₂CF₃ | CH₂CH₃ |
| CH₂—CH(CH₃)₂ | CH₃ |
| CH₂—CH(CH₃)₂ | CH₂CH₃ |
| CH₂—C(CH₃)₃ | CH₃ |
| CH₂—C(CH₃)₃ | CH₂CH₃ |
| CH(CH₃)₂ | CH₃ |
| CH(CH₃)₂ | CH₂CH₃ |
| t-Butyl | CH₃ |
| t-Butyl | CH₂CH₃ |
| Phenyl | CH₃ |
| Phenyl | CH₂CH₃ |
| 2-Pyridinyl | CH₃ |
| 2-Pyridinyl | CH₂CH₃ |
| 3-Pyridinyl | CH₃ |
| 3-Pyridinyl | CH₂CH₃ |
| 4-Pyridinyl | CH₃ |
| 4-Pyridinyl | CH₂CH₃ |
| Cyclopropyl | CH₃ |
| Cyclopropyl | CH₂CH₃ |
| Cyclopentyl | CH₃ |
| Cyclopentyl | CH₂CH₃ |
| Cyclohexyl | CH₃ |
| Cyclohexyl | CH₂CH₃ |

We claim:

1. A process for preparing 4-alkanoylaryl benzyl ether of the formula I

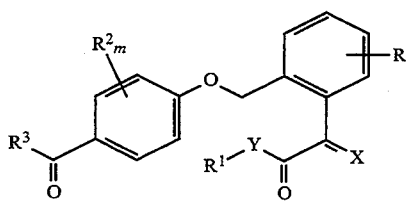

wherein

R is hydrogen, halogen, cyano, $C_1$–$C_4$-alkyl, or $C_1$–$C_4$alkoxy;

X is $CH_2$, CH—$CH_3$, CH—$CH_2$—$CH_3$, CH—$OCH_3$ OR N—$OCH_3$;

Y is oxygen, sulfur, direct linkage or nitrogen which can carry a hydrogen atom, a $C_1$–$C_4$-alkyl group or a $C_1$–$C_4$-alkoxy group;

m is 0, 1, 2 or 3, it being possible for the $R^2$ radicals to be different when m is 2 or 3;

$R^1$ is hydrogen; $C_1$–$C_5$-alkyl, $C_3$–$C_5$-alkenyl, $C_3$–$C_5$-alkynyl or $C_1$–$C_4$-alkoxy, it being possible for these groups to carry one or two halogen atoms;

$R^2$ is cyano, halogen, $C_1$–$C_4$-alkyl, $C_1$–$C_4$-alkoxy or $C_1$–$C_4$-haloalkyl;

$R^3$ is $C_1$–$C_{12}$-alkyl; $C_1$–$C_{12}$-haloalkyl; $C_3$–$C_8$-cycloalkyl; or an unsubstituted or substituted mono- to trinuclear aromatic system which may, besides carbon atoms, contain one to four nitrogen atoms or one to three hetero atoms selected from the group consisting of two nitrogen atoms and one oxygen or the group consisting of two nitrogen atoms and one sulfur atom, it also being possible for the aromatic radicals to carry one to three substituents each the same or different and selected from the groups consisting of halogen, $C_1$–$C_4$-alkyl, and $C_1$–$C_4$-alkoxy; which comprises reacting an aryl benzyl ether of the formula II

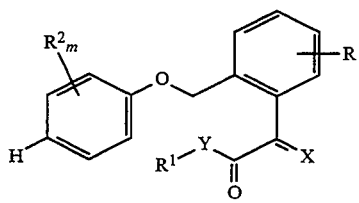

where X, Y, R, $R^1$, $R^2$ and m have the abovementioned meanings, with a carbonyl halide of the formula $R^3$—CO—halogen or with a carboxylic anhydride of the formula $R^3$—COO—CO—$R^3$ or with a carboxylic sulfonic anhydride of the formula $R^3COO$—$SO_2$—$R^4$ where $R^3$ has the abovementioned meaning, and $R^4$ is $C_1$–$C_4$-alkyl, $C_1$–$C_4$-haloalkyl or aryl, in the presence of an acid and in the presence or absence of a diluent.

2. A process as claimed in claim 1, wherein the reaction is carried out at from −80° C. to +140° C.

3. A process as claimed in claim 1, wherein said acid is a Lewis acid selected from the group consisting of $AlCl_3$, $AlBr_3$, $ZnCl_2$, $ZnBr_2$, $FeCl_3$, $FeBr_3$, $TiCl_4$, $SnCl_4$, $GaCl_3$, $InCl_3$ and $BF_3$.

4. A process as claimed in claim 1, wherein said acid is a Brösted acid selected from the group consisting of trifluoromethanesulfonic acid, methanesulfonic acid, polyphosphoric acid and sulfuric acid.

5. A process as claimed in claim 1, wherein said acid is an ion exchange resin with sulfo groups.

6. A process as claimed in claim 1, wherein said acid is an acid zeolites or a sheet zeolite selected from the group consisting of zeolite ZSM, Montomorillonit KSF and Montmorillonit K10.

7. A process as claimed in claim 3, wherein the Lewis acids are bound in the form of the metal compounds to an inert carrier selected from the group consisting of alumina, silica, active carbon, sheet-silicates and zeolites.

* * * * *